(12) United States Patent
Alsaffar

(10) Patent No.: US 6,389,602 B1
(45) Date of Patent: May 21, 2002

(54) THIN WALLED ELASTIC POLYURETHANE ARTICLES

(75) Inventor: Eman Alsaffar, Bury St. Edmunds (GB)

(73) Assignee: LRC Products Limited, Broxbourne (GB)

(*) Notice: Subject to any disclaimer, the term of this patent is extended or adjusted under 35 U.S.C. 154(b) by 0 days.

(21) Appl. No.: 09/265,573

(22) Filed: Mar. 10, 1999

(51) Int. Cl.⁷ .................. A41D 19/015; A61F 6/04; B29D 22/04; B29D 31/00

(52) U.S. Cl. ............. 2/161.7; 428/36.8; 428/36.9; 524/591; 604/349

(58) Field of Search .............. 428/36.8, 36.9; 2/161.7; 604/349

(56) References Cited

U.S. PATENT DOCUMENTS

| | | | |
|---|---|---|---|
| 4,239,879 A | 12/1980 | Fabris et al. | 528/76 |
| 4,917,850 A | 4/1990 | Gray | 264/301 |
| 5,100,922 A | 3/1992 | Wada et al. | 521/51 |
| 5,100,997 A | 3/1992 | Reisch et al. | 528/60 |
| 5,116,931 A | 5/1992 | Reisch et al. | 528/59 |
| 5,124,425 A | 6/1992 | Higuchi et al. | 528/59 |
| 5,250,582 A | 10/1993 | Hire et al. | 521/157 |
| 5,300,535 A | 4/1994 | Takeyasu et al. | 521/137 |
| 6,017,997 A * | 1/2000 | Snow et al. | 524/591 |

FOREIGN PATENT DOCUMENTS

| | | | |
|---|---|---|---|
| DE | 19708451 A1 * | 9/1998 | C08L/75/04 |
| DE | 19708451 | 9/1998 | |
| EP | 0573206 | 12/1993 | |
| EP | 0741152 A1 * | 6/1996 | C08G/18/08 |
| EP | 0741152 | 11/1996 | |
| EP | 0781791 | 7/1997 | |
| GB | 1401986 | 8/1975 | |
| GB | 2159526 | 12/1985 | |
| GB | 2174709 | 12/1986 | |

OTHER PUBLICATIONS

Barksby et al, "Novel Polyethyer . . . ", Polyurethan Tech., Feb. /Mar. '96, pp 36, 38, 40, 41, 42, 44, 1966.*

Acclaim Bulletin, ARCO Chemical Company, 1996.

Novel polyether polyols yield high–performance case elastomers—Barksby, Seneker, and Allen, *Urethanes Technology*, 1996, Feb./Mar., 36–44.

New Polyether Polyols for Aqueous Polyurethane Dispersions—Seneker, Barksby, and Ellerbe, UTECH Asia '97 Conference, Singapore, Feb. 1997.

* cited by examiner

*Primary Examiner*—Harold Pyon
*Assistant Examiner*—Sandra M. Nolan
(74) *Attorney, Agent, or Firm*—Stevens, Davis, Miller & Mosher, L.L.P.

(57) ABSTRACT

Soft, thin-walled elastic articles such as condoms and gloves are made of films of a linear polyurethane which has been so made as to have physical properties close to those of a similar film of natural rubber. The polyurethane is made from poly(propylene glycol) polyols with no more than 0.01 milliequivalents unsaturation per gram, and has a molecular weight Mn of 90 to 150 kg/mol, a ratio Mw:Mn of 1.2 to 2.2, and a ratio of hard:soft segments of 20:80 to 40:60. The film has an S100 of less than 2.0 MPa, an elongation at break of at least 800%, and a tensile strength of above 15 MPa.

18 Claims, 1 Drawing Sheet

THIN WALLED ELASTIC POLYURETHANE ARTICLES

Figure 1:
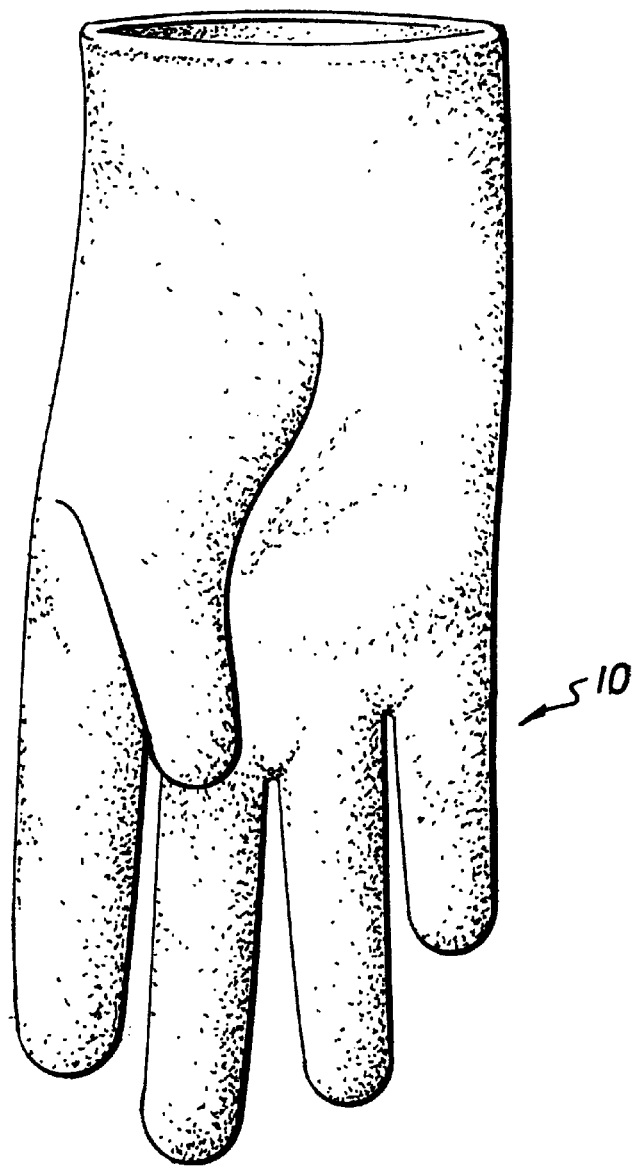

This invention relates to thin walled polyurethane elastic articles and to a method of making them.

Many devices for biomedical applications require the use of soft thin walled elastic articles. Examples of such articles are gloves for surgical operations and examinations under clean room conditions, and balloons for catheters and condoms. Natural rubber from latex is currently the material of choice for these types of applications due to its outstanding balance of mechanical properties. Typical properties are high elongation at break (800–900%), low modulus [a modulus at 100% elongation of 0.7–0.9 MPa], acceptable tensile strength (20–35 MPa) and a low degree of creep. Natural rubber does, however, have the drawback that the presence therein of proteins and other undesirable compounds, such as vulcanisation accelerator residues, can lead to human allergic reactions if these compounds are leached from the rubber network during use. Another potential hazard is the formation of nitrosamines which are suspect carcinogens. It would therefore be beneficial to replace natural rubber with a synthetic elastomer for the fabrication of articles for biomedical applications.

Polyurethanes have been used to fabricate thin walled elastic articles, usually by dip coating from organic solvent based solutions. However, these solutions are usually quite viscous, due to the high molecular weight of the polymers, and this often presents problems with processing. The molecular weight of a polyurethane elastomer is a key parameter to performance, particularly in regard to the physical properties of the material which will be poor if a suitably high molecular weight is not attained.

Quite apart from these general problems of using polyurethanes to fabricate thin walled elastic articles, there are further difficulties in using them as a replacement for natural rubber. Whilst, in general, polyurethane films can be made of good tensile strength (e.g. 30 to 60 MPa) and moderate elongation (450–650%), these known materials are much harder than natural rubber and will normally have a significantly higher modulus at 100% extension (hereinafter "S100"), for example of at least 2.2 and often much higher. Attempts to make softer polyurethanes have resulted in a lower modulus, but tensile strength and elongation at break have also been reduced and, most importantly, there has been an unacceptable loss in elasticity. Thus, it has not been possible to date to provide a polyurethane dipped film whose physical properties have been close to those of natural rubber.

European patent application 0741152 describes aqueous polyurethane dispersions based on polyether polyols of low unsaturation or monol content. The use of such polyols having an unsaturation of less than 0.02 meq/g polyol and preferably less than 0.01 meq/g polyol, is described as providing polyurethane dispersions of better properties. For example, substitution of the low unsaturation polyols for conventional polyols is shown to give films (cast on glass plates) having higher tensile strength, higher 100% and 300% moduli, and lower ultimate elongation.

European patent 0781791 also describes the use of low unsaturation copolymer polyols for making polyurethane elastomers. The unsaturation is 0.06 meq KOH/g or less, and the polyols are polyoxyalkylene polyether block copolymers. A principle use of the polyurethanes is for sealants and adhesives.

We have now found that by using certain low unsaturation polyols in a limited range of polyurethane polymers, it is possible to make soft thin-walled elastic polyurethane articles with physical properties very similar to such articles made of natural rubber.

In one aspect, the invention provides a soft, thin-walled elastic article made of a linear polyurethane having physical properties close to those of natural rubber wherein the article is made of a linear polyurethane which comprises an $\alpha,\omega$-dihydroxy polyol selected from poly(propylene glycol)s, said polyol containing no more than 0.01 milliequivalents unsaturation per gram; an aliphatic diisocyanate; and a chain extender; said polyurethane having a ratio of hard:soft segments from 20:80 to 40:60, a number average molecular weight (Mn) of from 90 to 150 kg/mole and a ratio of average molecular weight (Mw) to Mn of from 1.2 to 2.2; and wherein the said film has an S100 of less than 2.0 MPa, an elongation at break of at least 800% and a tensile strength of above 15 MPa.

In another aspect, the invention provides a method of making a soft, thin walled glove or condom of a linear polyurethane have properties close to those of natural rubber, which comprises dipping a former in an organic solution or aqueous dispersion of a linear polyurethane which comprises $\alpha,\omega$-dihydroxy polyol selected from poly(propylene glycol)s, said polyol containing no more than 0.01 milliequivalents unsaturation per gram; an aliphatic diisocyanate; and a chain extender; said polyurethane having a ratio of hard:soft segments from 20:80 to 40:60; a number-average molecular weight (Mn) of from 90 to 150 kg/mole and a ratio of average molecular weight (Mw) to Mn of from 1.2 to 2.2; drying the coated former and removing the glove or condom therefrom.

As used herein, the term "polyurethane" includes "polyurethane-urea".

The polyurethanes of the invention are linear and are made from one or more isocyanates, one or more polyols and one or more chain extenders. The polyols are polyether polyols based on propylene glycol and thus are $\alpha,\omega$-dihydroxy polyols. They preferably have a molecular weight of from 400 to 12000 daltons.

The polyurethanes of the invention can be made either by the so-called "one-shot" bulk polymerisation method, or by chain extending prepolymers.

The general method of preparation of the novel polyurethanes is conventional and, as such, will be well known to those skilled in that art. In general, we prefer to use the prepolymer method because it provides good control over hard/soft segment proportions and over product quality.

In order to achieve good physical properties in polyurethanes, high molecular weights are needed. It has been recognised in the art that $\alpha,\omega$-hydroxy polyols sometimes contain monohydroxy terminated species (called "monols") as impurities. These monols have only one hydroxy terminal and prevent the formation of high molecular weight products. The occurrence of monols in polyols can be reduced by using certain organometallic catalysts in the preparation, so that the polyol has only about 0.02 milliequivalents/g of unsaturation, but even this low level is not without effect. According to a feature of the present invention, we use $\alpha,\omega$-hydroxy polyols which contain no more than about 0.01, and most preferably no more than about 0.007, milliequivalents unsaturation per gram. Materials of this specification are available commercially. For example, Lyondell Chemical Co. (USA) supply "Acclaim" polyols which are said to have a very low level of monol impurity. These "Acclaim" polyols are for use in making high performance cast polyurethane elastomers to meet requirements not met by conventional rubbers and plastics, e.g. to provide high performance flexibility and toughness. Their utility in the present invention, in contributing to the production of polyurethanes closely matching natural rubber, is quite different from their proposed use for cast polyurethanes and, indeed, it is surprising that they are useful for the quite different purpose of the present invention.

Aliphatic diisocyanates are used to make the polyurethanes of the invention, since aromatic diisocyanates tend to give products of too high stiffness and creep to match natural rubber. Among the aliphatic diisocyanates which can be used is 4,4'-methylenebis(cyclohexyl isocyanate) (HMDI), available commercially as Desmodur W from Bayer. Others include isophorone diisocyanate (3-isocyanatomethyl-3,5,5-trimethylcyclohexyl isocyanate IPDI), available from Veba; hexamethylene diisocyanate (HDI) available from Bayer; cyclohexane-1,4-diisocyanate (CHDI) available as a development product from AKZO; cyclohexane-1,4-bis (methylene isocyanate) (BDI) available as a development product from Eastman; 1,3-bis(isocyanatomethyl) cyclohexane (HXDI) available from Takeda; TMDI, a mixture of 1,6-diisocyanato-2,2,4,4-tetramethylhexane and 1,6-diisocyanato-2,3,4-trimethylhexane available from Veba; and the meta and para isomers of tetramethylxylene diisocyanate which are available as TMXDI from American Cyanamid.

The most preferred diisocyanates are alicyclic diisocyanates such as, for example, 4,4'-methylenebis(cyclohexyl isocyanate) available as Desmodur W.

Aliphatic diisocyanates generally form polyurethanes which are non-yellowing, and this is an advantage with soft thin walled elastic articles.

In general, the isocyanates used in the present invention are bifunctional (i.e. diisocyanates) and are of sufficient reactivity to give the desired high molecular weight polyurethanes, with the desired elasticity. The optimum choice of isocyanate will, of course, depend on the choice of polyol and of chain extender, and the proportions used, as will be clear to those skilled in the art. When butanediol is used as chain extender, we particularly prefer to use Desmodur W as the isocyanate.

The nature of the chain extender can vary quite widely. We prefer to use bifunctional compounds, i.e. diols, and suitable examples include ethane-1,2-diol, propane-1,2-diol, propane-1,3-diol, butane-1,4-diol, hexane-1,6-diol, 2,3-dimethylbutane-2,3-diol, 2,5-dimethylhexane-2,5-diol. A preferred chain extender is butane-1,4-diol. Where the polyurethane is to be used in aqueous dispersion, a chain extender containing a sulphonic acid group or carboxylic acid group, such as dimethylolpropanoic acid, is preferred. In addition, diamines and hydroxyamines may be used as chain extenders to generate poly(urethane-ureas). Examples of such chain extenders are ethylenediamine, propane-1,3-diamine, propane-1,2-diamine, butane-1,4-diamine, 2-methylpentane-1,5-diamine, hexane-1,6-diamine, ethanolamine, 1-aminopropan-2-ol, 3-aminopropan-1-ol, 2-aminopropan-1-ol, 2-aminobutan-1-ol and 4-aminobutan-1-ol. Use of amino compounds to prepare poly(urethane ureas) can have the drawback of restricting the solubility of the polymer to highly polar high boiling solvents such as dimethylformamide (DMF), N-methylpyrrolidone (NMP) and dimethyl sulphoxide (DMSO).

The proportions of isocyanate, and polyol and chain extender which are used will, of course, affect the proportions of hard and soft segments in the polyurethane, and the molecular weight. In general, the ratio hard:soft segment will be from 20:80 to 40:60.

The preferred method of preparation involves first reacting n mole equivalents of the polyol with n+1 mole equivalents of the diisocyanate to form a prepolymer. Thus, the weight ratios of polyol to diisocyanate will depend on the molecular weights of the reactants. By way of an example, if 1 mole equivalent of a polyol of molecular weight 2,000 is reacted with 2 mole equivalents of a diisocyanate such as HMDI of molecular weight 262, then the weight ratio of polyol to diisocyanate in the prepolymer is slightly less than 4 to 1. If the prepolymer is then extended with 1 mole equivalent of a diol, such as butanediol (molecular weight 90), the overall weight percentages of components in the final polyurethane will be 76% polyol, 20% diisocyanate, 4% extender. By way of a further example, if 2 mole equivalents of the same polyol are reacted with 3 mole equivalents of the same diisocyanate, the weight ratio of polyol to diisocyanate in the prepolymer will be approximately 5.1 to 1. If this prepolymer is now extended with 2 mole equivalents of the same diol and 1 mole equivalent of the same diisocyanate, then the overall weight percentages of components in the final polyurethane will also be 76% polyol, 20% diisocyanate and 4% extender.

In general, the proportions by weight of polyol, isocyanate and extender will be:

|  | polyol | isocyanate | extender |
| --- | --- | --- | --- |
| general: | 50–85 | 10–30 | 1–15 |
| preferred | 70–80 | 15–25 | 2–7 |
| more preferred | 76 | 20 | 4 |

The number average molecular weights ($M_n$) of the polyurethanes of the invention will generally be in the range 90 to 150 kg/mole, preferably from 100 to 120. The spread of molecular weight as determined by the ratio $M_w:M_n$ is generally from 1.2 to 2.2, preferably 1.4 to 1.8. ($M_w$ is the weight average molecular weight.) As will be clear to those skilled in the art, the molecular weight of the polyurethane can be controlled by routine measures in the production process.

The polyurethanes of the present invention are closely matched to natural rubber in tensile properties. In this connection, the polyurethanes will generally have a S100 of less than 2.0 MPa, and most preferably less than 1.0 MPa, an elongation at break of at least 800%, and preferably above 1000%, and a tensile strength of above 15 MPa, and most preferably above 20 MPa. Polyurethanes with these particular combinations of properties so that they can be used in place of natural rubber, are novel.

Films of the invention are preferably made from organic solvent solutions or from aqueous dispersions of the polyurethanes, in conventional fashion such as by casting or dip coating. For solution fabrication, any suitable organic solvent can be used but we generally prefer to use tetrahydrofuran, although butan-2-one, γ-butyrolactone or aprotic solvents such as dimethyl formamide, dimethyl acetamide and N-methyl pyrrolidone may be used depending on the polyurethane structure. The aprotic solvents can be used in conjunction with a small amount of an inorganic halide such as 1 to 3% of lithium bromide. Alternatively, a small proportion of a non-solvent for the polyurethane may be used in conjunction with an appropriate solvent; these may include acetone, methyl isobutyl ketone, methylene chloride and chloroform, for example. The solutions can vary in the solids content but, for making articles such as gloves or condoms, the solids contents will usually be from about 10 to 30%, more usually from 15 to 20%. Films of the invention normally have a thickness of from 20 to 250 μm, preferably 35 to 150 μm for condoms and 100 to 200 μm for gloves.

The production of polyurethanes with the unique combination of properties described is surprising. It would have been expected in the art that at the level of hard segment content used in the present invention, the resulting polyurethane would be much harder and of lower elongation at break than has actually been found. The combination of properties which are actually found is surprising and highly advantageous in its close match to the properties of natural rubber.

In order that the invention may be more fully understood, the following Examples are given by way of illustration only.

EXAMPLE 1

A polyurethane of the invention was made by the prepolymer method by taking 198 g of a polypropylene glycol (Acclaim 2200), having a molecular weight of 1975 and a monol content of $6.2 \times 10^{-3}$ milliequivalents per gram, and reacting it with 52.8 g of HMDI at 55–60° C. in the presence of 0.2 g dibutyl tin dilaurate as catalyst. After a reaction time of 2 hours, a determination for the isocyanate content of the reaction mixture was made by a standard back titration of dibutylamine. The result of the NCO titration (approximately half that of the 6.7% by weight in the original reaction mixture) is used to determine the weights of chain extenders to be added to complete the reaction. Thus, 12.1 g of butanediol and 17.6 g of HMDI (a 2:1 molar ratio) were added to the reaction mixture which was heated and stirred until the reaction exotherm had reached 93° C. At this time the reaction mixture was poured into teflon coated trays and the polymer allowed to cure for 3 hours at 110° C.

The resulting polyurethane had 29% overall hard segment, $M_n$ 131 kg/mol and $M_w:M_n$ 1.5. The mechanical properties of a dipped thin film were 17.2 MPa tensile strength, 1.2 MPa S100, and 1330% elongation at break. The solution had a viscosity of 250 cps and a solids content of 18%.

EXAMPLE 2

An equivalent polyurethane based on a conventional polypropylene glycol was prepared by reacting 225 g of polypropylene glycol (ex Aldrich Chemicals) having a molecular weight of 2015, monol content of 0.045 milliequivalent per gram, with 58.7 g of HMDI. The reaction was carried out for 2 hours at 60° C. in the presence of dibutyl tin dilaurate as catalyst. After carrying out an isocyanate determination, the prepolymer was then chain extended with 18.3 g butanediol and 26.6 g HMDI (in the molar ratio of 2:1 respectively). The reaction was allowed to exotherm to 95° C. whereupon the polymer was poured into teflon coated trays and cured at 110° C. for 3 hours.

The resulting polyurethane had 30% hard segment, $M_n$ of 34 kg/mole and $M_w:M_n$ of 1.89. The mechanical properties of a dipped thin film were 4.5 MPa tensile strength, 2.4 MPa S100 and 620% elongation at break. Thus, the value of using a polyol with low monol end group impurities is clearly demonstrated from the above examples.

EXAMPLE 3

Another polyurethane was prepared using the same reactants as in Example 1 except that ethylene glycol was substituted for butanediol as a chain extender. In this case, 202 g of polyol was reacted with 52.2 g of HMDI at 55–60° C. to form a prepolymer. After carrying out an isocyanate determination, the prepolymer was extended by adding 11.6 g of ethylene glycol and 24.6 g of HMDI, the reaction conditions being the same as those in Example 1.

The resulting polyurethane had $M_n$ 125 kg/mole and $M_w:M_n$ of 1.5. The mechanical properties of a dipped thin film of this material were 29.5 MPa tensile strength, 1.23 MPa S100 and 920% elongation at break.

EXAMPLE 4

A polyurethane-urea was prepared using the same reactants as in Example 1 but ethanolamine was substituted for butanediol as a chain extender. 280.8 g of polyol was reacted with 74.6 g of HMDI at 60° C. to form a prepolymer. After carrying out an isocyanate determination, the prepolymer was extended by adding 8.5 g of ethanolamine to the reaction mixture and continuing stirring until the reaction exotherm had reached 100° C. The reaction mixture was then transferred to Teflon-coated trays and allowed to cure at 110° C. for 3 hours.

The resulting polyurethane urea had 23% hard segment, $M_n$ 109 kg/mol and $M_w/M_n$ 1.6. The mechanical properties of a thin film, dipped from a 9% w/w solution of this material in THF, were 31 MPa tensile strength, 1.4 MPa $S_{100}$ and 1020% elongation at break. The solution had a viscosity of 100 cP at a concentration of 15% w/w.

EXAMPLE 5

Higher molecular weight polyols can also be used to synthesize polyurethanes of the invention. A polyurethane of this type was prepared by taking 291.7 g of polypropylene glycol (Acclaim 3200), having a molecular weight of 2967 and a monol content of $5 \times 10^{-3}$ milliequivalents per gram, and reacting it with 77.35 g of HMDI in the presence of 0.1 g of dibutyl tin dilaurate. In this case a large excess of HMDI was used (3:1 molar ratio) to ensure that the higher molecular weight polypropylene glycol used would react completely to form an isocyanate capped prepolymer.

After a reaction time of 3 hours at 60° C., the isocyanate content of the reaction mixture was found to have decreased from 6.7% to 4.0%. The prepolymer was then extended by addition of 15.4 g of butane diol and the reaction mixture stirred until the temperature had reached 90° C., whereupon the polymer was transferred to Teflon-coated trays and cured at 110° C. for 5 hours.

The resulting polyurethane had 24% hard segment, $M_n$ of 146 kg/mole and $M_w/M_n$ of 1.5. The tensile properties of a thin film, dipped from a 15% solution of this material in THF, having a viscosity of 535 cP, were found to be 21 MPa tensile strength, 1.4 MPa $S_{100}$ and 1120% elongation at break.

EXAMPLE 6

Aliphatic diisocyanates are preferred to aromatic diisocyanates to synthesize polyurethanes of the invention as the use of aromatic diisocyanates tends to produce harder (higher $S_{100}$) elastomers. This is illustrated by the following example. An aromatic polyether urethane was synthesized by reacting 196.8 g (0.097 mole) of polypropylene glycol (Acclaim 2200) having a molecular weight of 2040, with a three-fold excess (75.6 g, 0.302 mole) of diphenyl methane diisocyanate (MDI) at 65° C. for 3 hours. This reaction was catalysed by the addition of 0.07 g of dibutyl tin dilaurate. After carrying out an isocyanate determination, this prepolymer was diluted with 354 g of THF and extended by addition of 16.94 g (0.188 mole) of butane diol. The chain extension reaction was allowed to proceed at 60° C. for 3 hours during which time a further 500 g of THF was added to control the viscosity of the polymer solution. The molecular weight of the resulting polyurethane, having 30% hard segment, was $M_n$ 81 kg/mol and $M_w/M_n$ 1.9. The mechanical properties of a polyurethane film cast from the solution were 23.6 MPa tensile strength, 3.1 MPa $S_{100}$ and 824% elongation.

Comparison of the mechanical properties of this elastomer with those of the polyurethane cited in Example 1 clearly demonstrates that use of an aromatic diisocyanate (MDI) has produced a stiffer (higher $S_{100}$) material with lower elongation at break.

EXAMPLE 7

Thin-walled elastic articles, such as condoms, were made from the polyurethanes of Examples 1 to 3 as follows. Solutions were prepared of 15–20% total solids of these polymers, in a solvent such as tetrahydrofuran, at a viscosity of 500–600 cps measured at 30° C. The solutions were degassed and allowed to equilibrate at room temperature for 2 hours. The thin-walled article was made by dipping a glass mandrel into the solution and then removing the mandrel therefrom to form a solution coated mandrel. This is allowed to set in the solution vapour layer prior to final drying in an oven for a specified length of time. Once drying is complete, the coated glass mandrel is placed in a cool water tank and allowed to hydrate for 20 minutes. The resulting dried thin-walled article is then removed from the glass mandrel.

The above process generally applies to all solvent based dipping of a thin walled article using both conventional polyurethanes as well as the polyurethanes of the invention. However, a solution of a polyurethane of the invention will generally have a lower viscosity than a polyurethane synthesized from a conventional polyol (polypropylene glycol) of equivalent molecular weight and solids content. This allows for dipped articles to be produced where the formation of defects such as holes (from bubbling) and uneven film thickness is avoided.

EXAMPLE 8

This Example and Example 9 illustrate aqueous polyurethane dispersions according to the invention. Acclaim 3210 (304.3 g), a polypropylene glycol with a monol content of $5 \times 10^{-3}$ milliequivalents per gram, was treated with 14.36 g of dimethylolpropanoic acid and 76 g of isophorone diisocyanate, in the presence of 0.1 g dibutyl tin dilaurate. After a reaction time of three hours at 80° C., the isocyanate content of the reaction mixture had decreased from 7.3% to 3.44%. The prepolymer was then neutralised with 7 g triethylamine in one hour at 60° C., prior to dispersion in water (with stirring) and chain extension with 8.75 g of ethylenediamine in water.

The resulting polyurethaneurea dispersion, having 24.6% hard segment, was cast or dipped to give a film, after drying, with mechanical properties: 15 MPa tensile strength, 1.6 MPa S100 and 1150% elongation at break.

EXAMPLE 9

In this Example, 264.4 g poly(tetramethylene glycol) of molecular weight 2051.2 was treated with 17.5 g dimethylolpropanoic acid and 88.61 g of HMDI in the presence of 0.1 g dibutyl tin dilaurate. After a reaction time of three hours at 80° C., the isocyanate content had decreased from 7.7% to 2.1%. The prepolymer was neutralised with 13.4 g triethylamine for one hour at 60° C. before stirring in water and chain extension with 4.8 g ethylenediamine in water.

The resulting dispersion was cast or dipped to give a film which, after drying, had mechanical properties: 15.5 MPa tensile strength, 1.8 MPa S100 and 947% elongation at break.

Figure 2:

In the accompanying drawing, FIG. 1 shows an embodiment of glove 10 of the invention and FIG. 2 shows an embodiment 20 of a condom of the invention. In both cases, the articles are made of a film of a polyurethane of the invention, the film having physical properties close to those of a similar film of natural rubber.

What is claimed is:

1. A thin-walled elastic article made of a linear polyurethane having physical properties close to those of natural rubber, wherein the article is made of a linear polyurethane which comprises the reaction product of an α,ω-dihydroxy polyol selected from poly(propylene glycol)s, said polyol containing no more than 0.01 milliequivalents unsaturation per gram; an aliphatic diisocyanate; and a chain extender; said polyurethane having a ratio of hard:soft segments from 20:80 to 40:60, a number average molecular weight (Mn) of from 90 to 150 kg/mole and a ratio of average molecular weight (Mw) to Mn of from 1.2 to 2.2; and wherein the said film has an S100 of less than 2.0 MPa, an elongation at break of at least 800% and a tensile strength of above 15 MPa.

2. An article according to claim 1, wherein the polyol contains no more than 0.007 meq/g unsaturation.

3. An article according to claim 1, wherein the aliphatic diisocyanate is selected from 4,4'-methylenebis (cyclohexylisocyanate), isophorone diisocyanate, hexamethylene diisocyanate, cyclohexane-1,4-diisocyanate, cyclohexane-1,4-bis(methylene isocyanate), 1,3-bis (isocyanatomethyl)cyclohexane, a mixture of 1,6-diisocyanato-2,2,4,4-tetramethylhexane and 1,6-diisocyanato-2,3,4-trimethylhexane, and tetramethylxylene diisocyanate.

4. An article according to claim 1, wherein the aliphatic diisocyanate is 4,4'-methylenebis(cyclohexyl isocyanate).

5. An article according to claim 1, wherein the chain extender is a diol, diamine or hydroxyamine.

6. An article according to claim 1, wherein the chain extender is butane-1,4-diol.

7. An article according to claim 1, wherein the chain extender contains a sulphonic acid group or carboxylic acid group.

8. An article according to claim 7, wherein the chain extender is dimethylolpropanoic acid.

9. An article according to claim 1, which is a medical examination glove, a surgeon's glove or a condom.

10. A method of making a thin walled glove or condom of a linear polyurethane having properties close to those of natural rubber, which comprises dipping a former in an organic solution or aqueous dispersion of a linear polyurethane which comprises the reaction product of an α,ω-dihydroxy polyol selected from poly(propylene glycol)s, said polyol containing no more than 0.01 milliequivalents unsaturation per gram; an aliphatic diisocyanate; and a chain extender; said polyurethane having a ratio of hard:soft segments from 20:80 to 40:60, a number average molecular weight (Mn) of from 90 to 150 kg/mole and a ratio of average molecular weight (Mw) to Mn of from 1.2 to 2.2; drying the coated former and removing the glove or condom therefrom.

11. A method according to claim 10, wherein the polyol contains no more than 0.007 meq/g unsaturation.

12. A method according to claim 10, wherein the aliphatic diisocyanate is selected from 4,4'-methylenebis(cyclohexyl isocyanate), isophorone diisocyanate, hexamethylene diisocyanate, cyclohexane-1,4-diisocyanate, cyclohexane-1,4-bis(methylene isocyanate), 1,3-bis(isocyanatomethyl) cyclohexane, a mixture of 1,6-diisocyanato-2,2,4,4-tetramethylhexane and 1,6-diisocyanato-2,3,4-trimethylhexane, and tetramethylxylene diisocyanate.

13. A method according to claim 10, wherein the aliphatic diisocyanate is 4,4'-methylenebis(cyclohexyl isocyanate).

14. A method according to claim 10, wherein the chain extender is a diol, diamine or hydroxyamine.

15. A method according to claim 10, wherein the chain extender is butane-1,4-diol.

16. A method according to claim 10, wherein the chain extender contains a sulphonic acid group or carboxylic acid group.

17. A method according to claim 16, wherein the chain extender is dimethylolpropanoic acid.

18. An article according to claim 1, wherein said film has an S100 of less than 1.0 MPa, and an elongation at break of at least 1000%.

* * * * *